United States Patent [19]

Fergéus et al.

[11] Patent Number: 6,086,597
[45] Date of Patent: Jul. 11, 2000

[54] OPHTHALMIC COMPOSITION

[75] Inventors: Susanna Fergéus, Björklinge; Kerstin Lundberg; Ove Wik, both of Uppsala, all of Sweden

[73] Assignee: Pharmacia & Upjohn AB, Stockholm, Sweden

[21] Appl. No.: 08/823,957

[22] Filed: Mar. 25, 1997

[30] Foreign Application Priority Data

Mar. 7, 1997 [SE] Sweden ................................. 9700827

[51] Int. Cl.$^7$ ...................................... A61F 9/00
[52] U.S. Cl. ............................. 606/107; 128/898
[58] Field of Search ................ 606/1, 107, 4–6, 606/166; 128/898

[56] References Cited

U.S. PATENT DOCUMENTS

| | | | |
|---|---|---|---|
| 4,978,352 | 12/1990 | Federov et al. | 606/166 |
| 5,112,350 | 5/1992 | Civerchia et al. | 606/166 |
| 5,273,056 | 12/1993 | McLaughlin et al. | |
| 5,562,676 | 10/1996 | Brady et al. | 606/107 |
| 5,604,244 | 2/1997 | DeSantis et al. | 514/317 |

FOREIGN PATENT DOCUMENTS

| | | |
|---|---|---|
| 0399156 | 11/1990 | European Pat. Off. |
| 0414373 | 2/1991 | European Pat. Off. |
| WO 9325187 | 12/1993 | WIPO |
| WO 9409795 | 5/1994 | WIPO |

OTHER PUBLICATIONS

International Search Report for PCT/SE98/00401 dated Jun. 26, 1998.

Black, *Ocular Surgery News International Edition*, pp. 1–4, Sep. 1996.

*Primary Examiner*—Glenn K. Dawson
*Attorney, Agent, or Firm*—Dinsmore & Shohl LLP

[57] ABSTRACT

Ophthalmic composition for use in ocular surgery includes an aqueous solution of sodium hyaluronate with a concentration within the range of 18–40 mg sodium hyaluronate/ml solution and the molecular mass of sodium hyaluronate being in the range of $1\times10^6$–$10\times10^6 < M >_{r,M}$. In a method for conducting ocular surgery, the composition is introduced into the eye as a surgical aid. The composition may be used in a method for conducting cataract surgery.

8 Claims, No Drawings

OPHTHALMIC COMPOSITION

OPHTHALMIC COMPOSITION

The present invention relates to an ophthalmic composition for use in ocular surgery and a method for conducting ocular surgery. In particular the invention relates to a composition of sodium hyaluronate with a specifically defined molecular mass and concentration, for use in ocular surgery.

Intraocular lens implantation has today become routine surgery. A major tool to accomplish this was the introduction of Healon® (1980), the high molecular mass, viscoelastic, noninflammatory preparation of sodium hyaluronate. Since then, the cataract surgery has undergone a tremendous progress and many viscoelastic products have been developed. Typically these products are aqueous solutions containing a polysaccharide such as sodium hyaluronate, sodium chondroitin sulfate and hydroxypropylmethylcellulose, at concentrations varying from 10–70 mg/ml. The molecular mass (expressed as mass average relative molecular mass, $<M>_{r,M}$) varies from about 20,000 (chondroitin sulfate) to about 5,000,000 (sodium hyaluronate).

A cataract surgery of today can be divided into several steps. The first step is pupil dilatation and local anaesthesia. The operation starts by making an incision into the anterior chamber of the eye. When the eye is punctured, the aqueous humour leaks out and the anterior chamber becomes shallow. A viscoelastic product is injected into the anterior chamber, which then regains its former shape and depth. The viscoelastic product maintains the anterior chamber and protects the vulnerable tissues, especially the endothelial cells on the cornea.

The next step is to make a hole in the anterior lens capsule, a capsulotomy, which can be done in several ways. The viscoelastic product helps the surgeon by creating enough space by maintaining the anterior chamber depth and stabilize the lens.

Extraction of the lens nucleus can be done in different ways, e.g. planned ECCE (extracapsular cataract extraction) or phacoemulsification (phaco) using ultrasound. The remaining lens cortex is removed by irrigation/aspiration.

After removal of the lens, viscoelastic product is again injected to inflate the capsular bag and to deepen the anterior chamber to make space for the intraocular lens implantation. The viscoelastic product maintains the space in the anterior chamber and is a very important protector of the endothelial cells and of other intraocular tissues from direct contact with the lens.

Upon completion of surgery, the viscoelastic product is removed from the eye by irrigation/aspiration and substituted by physiological salt solution. If needed the wound is sutured.

Planned ECCE is the term normally used when the lens nucleus is removed in one piece. Planned ECCE requires an incision size of 9–12 mm.

In the method by phaco the lens nucleus is disintegrated with the help of ultrasound and is aspirated through a small incision, usually approximately 3 mm. An intraocular lens, foldable or not foldable, is then implanted through the incision. Phaco is the most modern method, which has increased rapidly in popularity due to the improved patient outcome. The small incision needed, reduces the amount of astigmatism induced by the surgery. Phaco is the most commonly employed technique in most countries and it will be the dominating technique for the foreseeable future.

The demands on the viscoelastic products used in the surgical steps mentioned above are different. Current viscoelastic products can be divided into two broad groups. The first is a group of highly viscous cohesive products containing high molecular mass polysaccharides that already at moderate concentrations (about 1 mg/ml) form a flexible entangled molecular network and which have a high zero-shear viscosity. The second group consists of lower zero-shear viscosity dispersive products containing low molecular mass polysaccharides in high (about 70 mg/ml) concentrations, which tend to disperse in the eye and which do not exhibit cohesive properties even at high concentrations.

The dispersive products typically contain high concentration (approximately. 70 mg/ml) of low molecular mass polysaccharides (average mass average relative molecular mass about 200,000). These products fracture easily and stay in the anterior chamber during the turbulent phacoemulsification procedure. However, these products have poor space maintaining properties. Furthermore, these products can not easily be removed from the anterior chamber at the close of surgery, and frequently require high pressure to expel from the syringe through an ophthalmic cannula into the anterior chamber.

The cohesive products contain high molecular mass polysaccharide (mass average relative molecular mass: 1 to 5 million) at low concentration (10–15 mg/ml). The latter products can easily be injected through thin cannulas, and exhibit good space-maintaining properties. They can also easily be extracted from the anterior chamber due to the cohesive properties. However, as a consequence of the cohesive properties, these products frequently leave the chamber as a chunk during the turbulent phacoemulsification procedure.

The cohesive viscoelastic products are used to displace and stabilize tissues and to pressurize the anterior chamber. However, there is a risk that they leave the eye too quickly during phaco and leave the endothelium not well protected. On the contrary, the dispersive viscoelastic products stay in the anterior chamber during phaco but do not stabilize tissues very well. So far none of the viscoelastic products available have been able to match all viscoelastic needs during cataract surgery with phacoemulsification and it has been assumed impossible to make such a product.

To achieve the optimal viscoelastic effect in all the surgical steps, U.S. Pat. No. 5,273,056 suggests use of different viscoelastic products in the various steps. U.S. Pat. No. 5,273,056 uses a combination of both cohesive and dispersive viscoelastic products. A similar solution has been suggested by Dr. Steve A. Arshinoff in the description of the "soft-shell" technique (Ocular Surgery News, International edition, vol. 14 no. 18 1996, p. 17, "Soft-shell" technique uses two types of viscoelastic products" reported by Harvey Black)

The object of the present invention is to obtain an improved ophthalmic composition for use in ocular surgery. Further, the object with the present invention is to present a viscoelastic product that could be used in all steps of cataract surgery, especially cataract surgery with phacoemulsification. The object of the present invention is to obtain a viscoelastic product which combines dispersive and cohesive qualities.

Yet a further object of the invention is an improved method of ocular surgery.

The objects of the invention are achieved by the composition and the method as described herein.

According to the present invention an ophthalmic composition for use in ocular surgery is obtained. The composition comprises an aqueous solution of sodium hyaluronate with a concentration within the range of 18–40 mg sodium hyaluronate/ml solution and the molecular mass of sodium hyaluronate being in the range of $1\times10^6$–$10\times10^6$ $<M>_{r,M}$.

According to a further aspect of the invention use of an aqueous solution of sodium hyaluronate with a concentration within the range of 18–40 mg sodium hyaluronate/ml solution and the molecular mass of sodium hyaluronate being in the range of $1\times10^6$–$10\times10^6$ $<M>_{r,M}$, for the manufacture of a composition for ocular surgery is obtained.

According to yet a further aspect of the invention a method for conducting ocular surgery is obtained. According to the method a composition comprising an aqueous solution of sodium hyaluronate with a concentration within the range of 18–40 mg sodium hyaluronate/ml solution and the molecular mass of sodium hyaluronate being in the range of $1\times10^6$–$10\times10^6$ $<M>_{r,M}$ is introduced into the eye as a surgical aid.

According to yet a further aspect of the invention a method for conducting cataract surgery in an eye having an anterior chamber, a posterior chamber and a lens capsule is obtained. The method comprises the following steps:

a) entering the anterior chamber by making an incision and injecting a composition comprising an aqueous solution of sodium hyaluronate with a molecular mass within the range of $1\times10^6$–$10\times10^6$ $<M>_{r,M}$ and a concentration within the range of 18–40 mg/ml into the anterior chamber;

b) performing a capsulotomy;

c) removing of lens and lens cortex;

d) injecting into the lens capsule the composition used in step a) and implanting an intraocular lens;

e) optionally, removing the composition injected in steps a) and d).

With the present invention it was surprisingly found that the composition according to the invention, with the increased concentration of the high molecular mass sodium hyaluronate, had an excellent performance in all steps of ocular surgery. The new hyaluronate composition is both cohesive and dispersive and stays in the anterior chamber during phaco emulsification. Because of these specific qualities the composition has a very good protecting effect against, as well mechanical damage, as against the free radicals which are formed by the ultrasound during the phacoemulsification procedure. The composition is also cohesive enough to maintain the anterior depth. The fact that the composition works well during the phacoemulsification step is surprising considering this composition is more cohesive than known sodium hyaluronate products on the market. A possible explanation to the obtained result is that by making the solution more cohesive, apparently a state is reached where the solution also becomes brittle. In highly turbulent flow (as during phaco), the solution close to the phaco instrument fractures, while a substantial amount of solution remains in the anterior chamber as a soft shell. The ophthalmic composition according to the invention has preferably a concentration within the range of 18–35 mg/ml, most preferably within 20–28 mg/ml and the molecular mass of the sodium hyaluronate is preferably within the range $1\times10^6$–$6\times10^6$ $<M>_{r,M}$, most preferably within $2.5\times10^6$–$5\times10^6$ $<M>_{r,M}$.

The ophthalmic composition according to the invention can be used in all types of ocular surgery, such as cataract surgery, glaucoma surgery, vitreous surgery and posterior segment surgery. The cohesive qualities of the present composition are very suitable in glaucoma, vitreous and posterior segment surgery both as a protector of eye tissue and to move and hold tissue away from the operation area and as an antiadherence product. However, the composition is especially suitable for cataract surgery with phacoemulsification. Thus, in a preferred embodiment of the present invention step c) in the above mentioned method is made by phacoemulsification. At the end of the surgery the composition according to the invention is preferably removed from the eye, but can be left in special cases.

The composition according to the invention is prepared in a conventional manner by dissolving the sodium hyaluronate in an aqueous solvent containing physiological amounts of sodium chloride to the required concentration of sodium hyaluronate. Sodium hyaluronate of suitable molecular mass is today a commercially available product. The solvent may also contain other inorganic salts such as calcium-, magnesium-and potassium chloride in physiological concentrations. Suitably the solvent may also contain buffering agents such as phosphate, acetate, carbonate or citrate in physiological concentrations. The solvent may also contain other physiological compounds. As mentioned above the composition has a good protecting effect against the free radicals produced during phaco. In order to increase this protective effect a compound acting as a scavenger can be added to the composition. As suitable scavengers can be mentioned superoxidedismutase (SOD), mannitol, glutathione or other known scavenger compounds acceptable to the eye.

The invention will now be illustrated with the following examples which however, are not intended to restrict the invention.

EXAMPLE 1

Two sodium hyaluronate solutions A and B were prepared accordingly:

| Solution A | |
|---|---|
| Sodium hyaluronate $<M>_{r,M} = 3 \times 10^6$ | 20 mg |
| Sodium chloride | 8.5 mg |
| Disodium phosphatedihydrate | 0.28 mg |
| Monsodium phosphatemonchydrate | 40 µg |
| Water suitable for injection solutions to obtain pH = 7.0–7.5 | 1 ml |
| Solution B | |
| Sodium hyaluronate $<M>_{r,M} = 3 \times 10^6$ | 25 mg |
| Sodium chloride | 8.5 mg |
| Disodium phosphatedihydrate | 0.28 mg |
| Monsodium phosphatemonohydrate | 40 µg |
| Water suitable for injection solutions to obtain pH = 7.0–7.5 | 1 ml |

These compositions were compared with the following commercially available products:

Viscoat® (Alcon Surgical Inc.)

Composition according to the manufacturer:

| | |
|---|---|
| Sodium chondroitin sulfate $<M>_{r,M} = 25,000$ | 40 mg/ml |
| Sodium hyaluronate | 30 mg/ml |

|                                   |             |
| --------------------------------- | ----------- |
| $<M>_{r,M}$ = 500,000             |             |
| pH = 6.2–7.8                      |             |

Amvisc Plus® (Chiron Vision):
Composition according to the manufacturer:

|                                   |             |
| --------------------------------- | ----------- |
| Sodium hyaluronate                | 16 mg/ml    |
| $<M>_{r,M}$ = 1.5 × 10$^6$        |             |
| pH = 6.4 (non-buffered)           |             |

HealonGV® (Pharmacia & Upjohn)
Composition according to the manufacturer:

|                                   |             |
| --------------------------------- | ----------- |
| Sodium hyaluronate                | 14 mg/ml    |
| $<M>_{r,M}$ = 5 × 10$^6$          |             |
| pH = 7.0–7.5                      |             |

Ocucoat® (Storz Ophthalmics,Inc.)
Composition according to the manufacturer:

|                                   |             |
| --------------------------------- | ----------- |
| Hydroxypropylmethylcellulose      | 20 mg/ml    |
| $<M>_{r,M}$ = 80,000              |             |
| pH = 6.8–7.5                      |             |

The solutions were tinted by fluorescein and filled in syringes. The materials were tested by an in-house excellent lab. technician and seven skilled ophthalmic surgeons, in masked trials, on pig and human cadaver eyes. The performance of all products in the different surgical steps and the overall assessment were established on a scale 0–100 where 0=worthless, 100=excellent:

| Step | Viscoat | Amvisc Plus | HealonGV | Solution B | Solution A | Ocucoat |
| --- | --- | --- | --- | --- | --- | --- |
| Injection | 16 | 93 | 93 | 74 | 85 | 80 |
| Capsulo rhexis | 70 | 56 | 79 | 93 | 83 | 33 |
| Phaco | 66 | 47 | 21 | 82 | 66 | 17 |
| IOL* | 66 | 73 | 96 | 91 | 98 | 25 |
| Removal | 21 | 51 | 93 | 65 | 86 | 20 |
| Overall | 42 | 45 | 59 | 86 | 88 | 30 |

*Intra ocular lens implantation

The result can also be visualized in the following way, where+denotes better than average and—worse than average:

|            | Injection | Capsulo rhexis | Phaco | IOL | Removal | Overall |
| ---------- | --------- | -------------- | ----- | --- | ------- | ------- |
| Viscoat    | −         | +              | +     | +   | −       | −       |
| Ocucoat    | +         | −              | −     | −   | −       | −       |
| Amvisc plus | +        | +              | −     | +   | +       | −       |
| Healon GV  | +         | +              | −     | +   | +       | +       |
| Solution A | +         | +              | +     | +   | +       | +       |
| Solution B | +         | +              | +     | +   | +       | +       |

From the result it is evident that both solution A and B according to the invention exhibit a very satisfactory performance in all steps of surgery.

EXAMPLE 2

Further sodium hyaluronate solutions according to the invention were prepared in the same manner as in example 1 with different molecular mass and concentrations. The solutions were tested by the skilled lab. technician or a skilled ophthalmic surgeon. The following overall assessment was obtained:

| Solution | Concentration (mg/ml) | $<M>_{r,M}$ (10$^6$) | Overall assessment |
| --- | --- | --- | --- |
| Solution C | 18 | 3.5 | 85 |
| Solution D | 19 | 1 | 100 |
| Solution E | 19 | 2 | 100 |
| Solution F | 35 | 1 | 100 |

From these result it is evident that other sodium hyaluronate solutions within the claimed range work equally well.

We claim:

1. A method for conducting cataract surgery in an eye having an anterior chamber, a posterior chamber and a lens capsule, the method comprising the following steps:

a) entering the anterior chamber by making an incision and injecting a composition comprising an aqueous solution of sodium hyaluronate into the anterior chamber, the aqueous solution having a concentration within the range of 18–40 mg sodium hyaluronate/ml solution and the sodium hayluronate having a molecular mass within the range of 2.5×10$^6$–10×10$^6$ $<M>_{r,M}$;

b) performing a capsulotomy;

c) removing lens and lens cortex;

d) injecting into the lens capsule the composition used in step a) and implanting an intraocular lens; and e) optionally, removing the composition injected in steps a) and d).

2. A method according to claim 1, wherein step c) is conducted by phacoemulsification.

3. A method according to claim 2, wherein the molecular mass of the sodium hayluronate is within the range 2.5×10$^6$–6×10$^6$ $<M>_{r,M}$ and the concentration of the aqueous solution is within the range of 18–35 mg/ml.

4. A method according to claim 2, wherein the molecular mass of the sodium hayluronate is within the range 2.5×10$^6$–5×10$^6$ $<M>_{r,M}$ and the concentration of the aqueous solution is within the range of 20–28 mg/ml.

5. A method according to claim 2, wherein the composition further comprises a compound acting as a scavenger.

6. A method according to claim 1, wherein the molecular mass of the sodium hyaluronate is within the range of 2.5×10$^6$–6×10$^6$ $<M>_{r,M}$ and the concentration of the aqueous solution is within the range of 18–35 mg/ml.

7. A method according to claim 1, wherein the molecular mass of the sodium hyaluronate is within the range of $2.5 \times 10^6 - 5 \times 10^6$ $<M>_{r,M}$ and the concentration of the aqueous solution is within the range of 20–28 mg/ml.

8. A method according to claim 1, wherein the composition further comprises a compound acting as a scavenger.

* * * * *